(12) United States Patent
Zhong et al.

(10) Patent No.: US 9,738,639 B2
(45) Date of Patent: Aug. 22, 2017

(54) PYRROLOQUINOLINE QUINONE LITHIUM SALT CRYSTAL AND PREPARATION METHOD AND APPLICATION THEREOF

(71) Applicant: SHANGHAI RI XIN BIOTECHNOLOGY CO., LTD., Shanghai (CN)

(72) Inventors: Chunjiu Zhong, Shanghai (CN); Xuefeng Mei, Shanghai (CN); Huan Zhang, Shanghai (CN)

(73) Assignee: Shanghai Ri Xin Biotechnology Co., Ltd. (CN)

( * ) Notice: Subject to any disclaimer, the term of this patent is extended or adjusted under 35 U.S.C. 154(b) by 5 days.

(21) Appl. No.: 14/897,926

(22) PCT Filed: Jun. 23, 2014

(86) PCT No.: PCT/CN2014/080542
§ 371 (c)(1),
(2) Date: Dec. 11, 2015

(87) PCT Pub. No.: WO2015/000370
PCT Pub. Date: Jan. 8, 2015

(65) Prior Publication Data
US 2016/0137641 A1    May 19, 2016

(30) Foreign Application Priority Data
Jul. 1, 2013   (CN) .......................... 2013 1 0270885

(51) Int. Cl.
*A61K 31/44*   (2006.01)
*C07D 471/04*   (2006.01)

(52) U.S. Cl.
CPC .................. *C07D 471/04* (2013.01)

(58) Field of Classification Search
CPC .................................................. C07D 471/04
See application file for complete search history.

(56) References Cited

U.S. PATENT DOCUMENTS

2010/0190815 A1   7/2010 Ogino et al.
2011/0313164 A1* 12/2011 Zhong .................. C07D 471/04
                                                                546/84

FOREIGN PATENT DOCUMENTS

| CN | 101193888 A | 6/2008 |
| CN | 101851234 A | 10/2010 |
| CN | 101885725 A | 11/2010 |
| JP | 2011-26812 A | 6/2011 |
| WO | WO 2008/029907 A1 | 3/2008 |

OTHER PUBLICATIONS

Kazuto et al (JP2011126812A, published Jun. 30, 2011, Machine Translation).*
Moulton et al (Chemical Review, 2001, 101, 1629-1658).*
Kobayashi et al., "Pyrroloquinoline quinone (PQQ) prevents fibril formation of α-synuclein", Biochemical and Biophysical Research Communications, 2006, 349, 1139-1144.
Nunome et al., "Pyrroloquinoline Quinone Prevents Oxidative Stress-Induced Neuronal Death probably through Changes in Oxidative Status of DJ-1", Biol. Pharm. Bull., Jul. 2008, 31(7), 1321-1326.

* cited by examiner

*Primary Examiner* — Jason Sims
*Assistant Examiner* — Ibrahim D Bori
(74) *Attorney, Agent, or Firm* — Baker & Hostetler LLP

(57) ABSTRACT

The present invention provides pyrroloquinoline quinone lithium salt crystal and a preparation method and application thereof. Characteristic absorption peaks appear when the diffraction angles are 6.222±0.2°, 7.379±0.2°, 7.941±0.2°, 23.631±0.2°, 24.044±0.2°, 25.497±0.2°, 27.541±0.2°, 30.736±0.2°, and 32.306±0.2° degrees in a powder X-ray diffraction pattern of the pyrroloquinoline quinine lithium salt crystal. The maximum value of thermal absorption of the pyrroloquinoline quinine lithium salt crystal appears between 90° C. and 96° C. through differential scanning calorimetry. Peaks appear when infrared spectroscopy of the pyrroloquinoline quinine lithium salt crystal is at 3396.03 $cm^{-1}$, 1652.70 $cm^{-1}$, 1604.48 $cm^{-1}$, 1500.35 $cm^{-1}$, 1355.71 $cm^{-1}$, 1243.86 $cm^{-1}$, 1147.44 $cm^{-1}$, 808.03 $cm^{-1}$, 761.74 $cm^{-1}$, and 570.83 $cm^{-1}$. The pyrroloquinoline quinine lithium salt polymorphism can be applied to preparation of medicines for curing memory damage.

11 Claims, 2 Drawing Sheets

PYRROLOQUINOLINE QUINONE LITHIUM SALT CRYSTAL AND PREPARATION METHOD AND APPLICATION THEREOF

CROSS-REFERENCE TO RELATED APPLICATIONS

The present application is a National Stage Application of International Application No. PCT/CN2014/080542, filed on Jun. 23, 2014, which claims priority to Chinese patent application No. 201310270885.2, filed on Jul. 1, 2013, and entitled "PYRROLOQUINOLINE QUINONE LITHIUM SALT CRYSTAL AND PREPARATION METHOD AND APPLICATION THEREOF", the entire disclosure of which is incorporated herein by reference.

TECHNICAL FIELD

The present invention is directed to a pyrroloquinoline quinine lithium salt crystal and preparation method and application thereof.

BACKGROUND

The full name of pyrroloquinoline quinine lithium salt is trilithium derivative of pyrroloquinoline quinine. Its formula is $C_{14}H_3N_2O_8Li_3$, and molecular weight is 348. It has the following chemical structural:

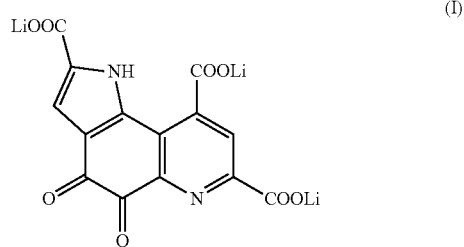

(I)

A substance with the same chemical composition may crystallize with two or more different spatial lattice arrangements. This phenomenon is called polymorphism. The polymorphic behavior of drugs can be of crucial importance in pharmacy and pharmacology, which takes tremendous impacts on drug quality. Varied crystalline forms may differ from each other with respect to one or more physical properties, such as crystal shape, melting point, hardness, solubility and dissociation, state stability and compaction behavior. The differences in physical properties exhibited by polymorphs affect pharmaceutical parameters such as storage stability, bioavailability and efficacy. Therefore, new drug R&D should give more attention to the research on drug polymorphism and crystalline control.

PQQ is discovered as water-soluble B-vitamin by Japanese scientists at 2003. Mice deprived of PQQ grew poorly, have friable skin, develop abnormalities as osteolathyrism, have impaired immune function, are failed to reproduce and are prone to arthritis. Therefore, PQQ is identified as an essential nutrient in vivo. It is thought that PQQ has the same effect on human. Current techniques publish that the molecular weight of PQQ is 330. It is early discovered in microorganism, and it also exists in higher eukaryotes. Its crystalline structure and chemical synthesis are already clarified.

PQQ is a cofactor of multiply essential enzymes. PQQ may ameliorate the function of mitochondrial respiratory chain and the levels of free radicals in vivo. Studies indicate that PQQ deficient mice grow poorly, are failed to reproduce and are prone to arthritis. Therefore, PQQ is identified as an essential vitamin and nutrient in vivo. Studies demonstrate that PQQ has the following functions related with nervous system: (1) Antioxidant: strongly scavenging reactive oxygen species; (2) Alteration of the function of respiratory chain: maintaining the energy metabolism of mitochondria; (3) Activation of signal pathway: stimulating the release of nerve growth factor, recovering and promoting the growth of nerve; (4) Regulating the growth of somatic cells and nerve; effectively preventing liver impairment; (5) Attenuating the deposition of α-synuclein protein and preventing the fibrosis of nerve cells. Therefore, PQQ exhibits beneficial effect on treating neurodegenerative diseases, such as Parkinson's disease and Alzheimer's disease (AD).

Pyrroloquinoline quinine lithium salt has been proved to suppress the glycogen synthase kinase-3 activities (GSK-3) and has potential value for treating several mental diseases. Therefore, we pay more attention to the adverse application values of pyrroloquinoline quinine lithium salt. We try to find out its multifactorial mechanisms and apply it on preventing mental illness

SUMMARY

The present invention is directed to pyrroloquinoline quinine lithium salt crystal and preparation method and application thereof.

The present invention discloses a crystal of pyrroloquinoline quinine lithium salt, characterized by an X-ray powder diffraction pattern with significant peaks at diffraction angles (2θ values) of about 6.222±0.2°, 7.379±0.2°, 7.941±0.2°, and 23.631±0.2°. Its endothermic peak is around 90-96° C. in the differential scanning calorimetry (DSC) thermogram. It shows peaks around 3396.03 $cm^{-1}$, 1652.70 $cm^{-1}$, 1604.48 $cm^{-1}$, and 1355.71 $cm^{-1}$ on infrared spectroscopy (IR) pattern.

In one embodiment, the pyrroloquinoline quinine lithium salt crystal is characterized by an X-ray powder diffraction pattern with more significant peaks at diffraction angles (2θ values) of about 24.044±0.2°, 25.497±0.2°, 27.541±0.2°, 30.736±0.2°, 32.306±0.2° and infrared spectroscopy (IR) pattern with more peaks around 1500.35 $cm^{-1}$, 1243.86 $cm^{-1}$, 1147.44 $cm^{-1}$, 808.03 $cm^{-1}$, 761.74 $cm^{-1}$, 570.83 $cm^{-1}$.

In a further embodiment, the compound stably exists as a nonahydrate by dynamic vapor sorption analysis. It forms monohydrate under the scope of relative humidity (RH) from 20% to 50%. It forms dihydrate under the scope of relative humidity (RH) from 70% to 100%.

In a still further embodiment, the compound shows an endothermic peak of 93.33° C. in the differential scanning calorimetry (DSC) thermogram.

The present invention is directed to the process of preparing the pyrroloquinoline quinine lithium salt crystal of the following method: pyrroloquinoline quinine is mixed with lithium hydroxide (weight ratio 4:1), followed by adding organic solvent for continuous stirring for 2 hours at 0-5° C., then acetonitrile is added to the mixture (the ratio of acetonitrile to pyrroloquinoline quinine is 8 mL: 4 g), followed by stirring for 1 hour, precipitated intermediate A of pyrroloquinoline quinine lithium salt is collected by filtration. The resultant intermediate A of pyrroloquinoline quinine lithium salt is dissolved in water, followed by adding tetrahydrofuran or isopropanol until complete mixed (the ratio of intermediate A of pyrroloquinoline quinine lithium salt, water and tetrahydrofuran or isopropanol is 10-1000 mg:0.5-20 mL:4-80 mL), the pyrroloquinoline quinine lithium salt crystal is obtained by standing overnight at room temperature.

In one embodiment, the organic solvent is selected from the group consisting of ketones, ethers, aliphatic hydrocarbons, aromatic hydrocarbons, esters, nitriles, alcohols, halogenated hydrocarbons, and a combination of two or more thereof, which dissolves the raw material and does not ruin its structure.

In a further embodiment, the organic solvent is selected from the group consisting of methanol, ethanol, isopropanol, pentanol, acetone, 2-butanone, tetrahydrofuran, nitromethane, acetonitrile, chloroform, dichloromethane, methyl tert-butyl ether and a combination of two or more thereof. The ratio of pyrroloquinoline quinine to organic solvent is 20 mg:1 mL.

The present invention is directed to a pharmaceutical composition comprising the pyrroloquinoline quinine lithium salt crystal and at least any one form pharmaceutically acceptable excipients.

In one embodiment, the pharmaceutically acceptable excipients are selected from fillers, disintegrants, binders, lubricants and a combination of two or more thereof.

In another embodiment, the fillers are selected from starch, lactose, crystalline cellulose, dextrin, mannitol, oxidase, calcium sulfate and a combination of two or more thereof.

In another embodiment, the disintegrants are selected from carboxymethylcellulose and its salt, crosslinked carboxymethylcellulose and its salt, crosslinked polyvinylpyrrolidone, sodium carboxymethyl starch, low-substituted hydroxypropylcellulose and a combination of two or more thereof.

In another embodiment, the binders are selected from polyvinylpyrrolidone, hydroxypropyl methyl cellulose, starch slurry and a combination of two or more thereof.

In another embodiment, the lubricants are selected from magnesium stearate, calcium stearate and a combination of two or more thereof.

The present invention provides the application of the pyrroloquinoline quinine lithium salt crystal on preparing medicaments for treating memory impairments.

The present invention discloses crystalline form B of pyrroloquinoline quinine lithium salt, wherein the X-ray powder diffraction pattern, differential scanning calorimetry (DSC) thermogram, dynamic vapor sorption (DVS) curve and infrared spectroscopy (IR) pattern are fundamentally consistent with FIG. 1, FIG. 2, FIG. 3 and FIG. 4, respectively.

Comparing with current technique, the present invention contains more beneficial effects:

The present invention is directed to the pyrroloquinoline quinine lithium salt crystal and preparation method and application thereof. The pyrroloquinoline quinine lithium salt crystal could be used for preparing medicaments for treating memory impairments

DETAILED DESCRIPTION OF THE DISCLOSURE

The embodiments of the present disclosure are described in the following through specific examples, and those skilled in the art can easily understand other advantages and effects of the present disclosure according to the content disclosed in the specification.

The foregoing and other objects, features and advantages of the invention will be apparent from the following more particular description of preferred embodiments of the invention, as illustrated in the accompanying drawings.

Laboratory Condition:

X-ray powder diffraction (XRPD) patterns of the polymorphs are measured on a Bruker D2 phaser X-ray powder diffractometer using Cu-Ka radiation at room temperature. The tube voltage and amperage ware set to 40 kV and 40 mA, respectively. A theta-two theta continuous scan at 0.2 sec/step from 3° to 40° is used.

In a further embodiment, the pattern of crystalline is characteristic in X-ray powder diffraction pattern. The band, especially in low angle, can be slightly changed in the relative intensity depending on crystallization condition, particle size, relative concentration of mixture and other measurement condition. Therefore, the relative intensity of diffraction angle 2θ of the crystalline form is not characteristic. The identification of crystalline form should be determined with the reference to the peak positions, but not their relative intensity. Additionally, the identification of crystalline form should not depend on one single peak, but comprehensive analysis of specific dI/II system. Moreover, during the identification of mixture, some deficiency of peak can occur due to the decline of sample concentration. Therefore, it is not necessary to find safe bands appeared in highly pure samples. Even a single band may identify the crystalline form.

Differential Scanning Calorimetry (DSC) thermograms of the polymorphs are measured on a DSC8500 (perkinelemer, USA). Analysis conditions are 10° C./min with a nitrogen purge.

Infrared spectroscopy (IR) patterns of the polymorphs are measured on a Nicolot-Magna FT-IR750 (Nicoiot-Magna, USA) under room temperature, scanning at 4000-350 $cm^{-1}$.

Dynamic Vapor Sorption (DVS) curves of the polymorphs are measured on SMS DVS Intrinsic at 0-95% RH and 25° C.

Figure 1:
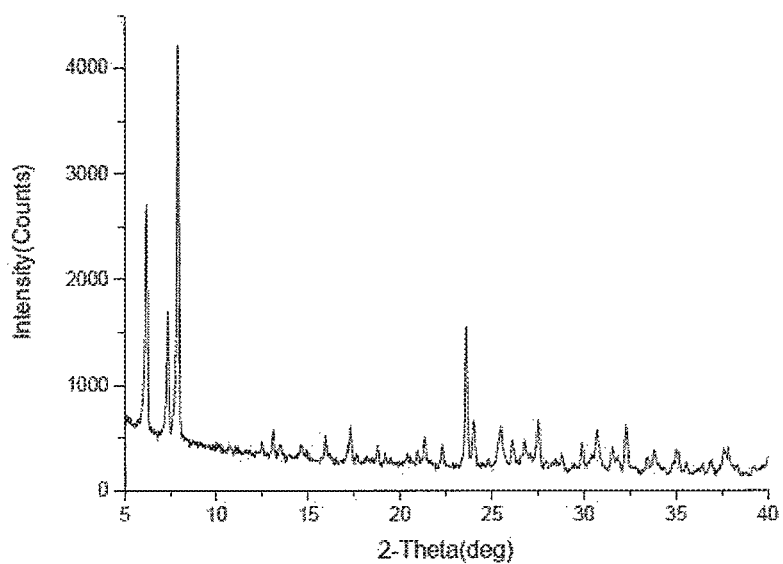
FIG. 1 is a characteristic X-ray Powder Diffraction (XRPD) pattern for pyrroloquinoline quinine lithium salt crystal.

Example 1: Preparation of Pyrroloquinoline Quinine Lithium Salt Crystal 4 g of pyrroloquinoline quinine is mixed with 1 g of lithium hydroxide, followed by adding 16 mL of $ddH_2O$. The mixture is stirring at 0-5° C. for 2 hours, and 8 mL of acetonitrile is added to the mixture, followed by stirring for 1 hour. Precipitated intermediate A of pyrroloquinoline quinine lithium salt is collected by filtration. The resultant 10 mg of intermediate A of pyrroloquinoline quinine lithium salt is dissolved in 0.5 mL of water, followed by adding tetrahydrofuran until complete mixed. The 1 mg of crystalline form B of pyrroloquinoline quinine lithium salt is obtained by standing overnight at room temperature. The obtained sample is measured by X-ray power diffraction as shown in FIG. 1.

The peak data of X-ray power diffraction pattern is described below:

TABLE 1

Peak data list of X-ray power diffraction pattern for crystalline form B of pyrroloquinoline quinine lithium salt

| 2θ° | d/A | Intensity % |
|---|---|---|
| 6.222 | 1850 | 59.7 |
| 7.379 | 844 | 27.2 |
| 7.941 | 3099 | 100 |
| 12.495 | 84 | 2.7 |
| 13.093 | 206 | 6.6 |
| 13.48 | 98 | 3.2 |
| 14.633 | 129 | 4.2 |
| 15.938 | 189 | 6.1 |
| 17.299 | 287 | 9.3 |
| 17.652 | 71 | 2.3 |
| 18.775 | 145 | 4.7 |
| 19.193 | 80 | 2.6 |
| 20.375 | 60 | 1.9 |
| 20.962 | 100 | 3.2 |
| 21.326 | 234 | 7.6 |
| 22.305 | 167 | 5.4 |
| 23.631 | 1184 | 38.2 |
| 24.044 | 403 | 13 |
| 25.497 | 321 | 10.4 |
| 26.146 | 187 | 6 |
| 26.801 | 189 | 6.1 |
| 27.541 | 372 | 12 |
| 28.461 | 62 | 2 |
| 28.817 | 120 | 3.9 |
| 29.909 | 209 | 6.7 |
| 30.736 | 328 | 10.6 |
| 31.59 | 186 | 6 |
| 31.833 | 89 | 2.9 |
| 32.306 | 397 | 12.8 |
| 33.461 | 138 | 4.5 |
| 33.843 | 202 | 6.5 |
| 35.059 | 215 | 6.9 |
| 35.561 | 86 | 2.8 |
| 36.42 | 70 | 2.3 |
| 36.893 | 95 | 3.1 |
| 37.633 | 208 | 6.7 |
| 38.315 | 75 | 2.4 |
| 39.231 | 48 | 1.5 |

Figure 2:
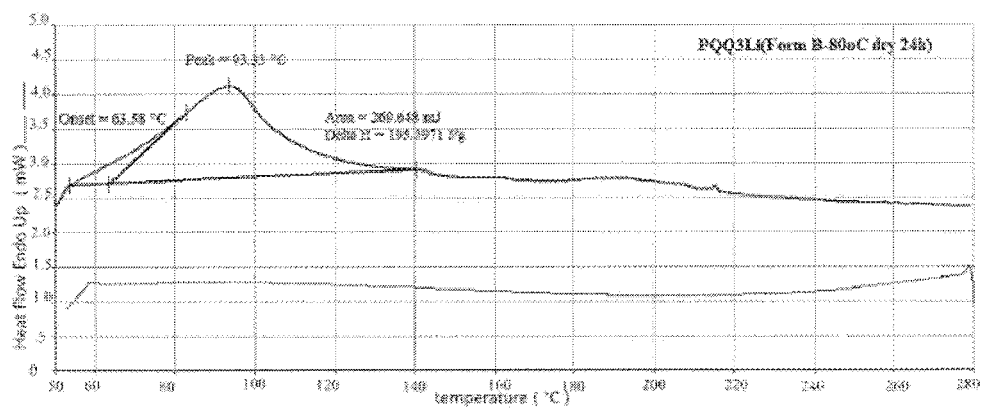
FIG. 2 is a characteristic Differential Scanning Calorimetry (DSC) thermogram for pyrroloquinoline quinine lithium salt crystal.
Figure 3:
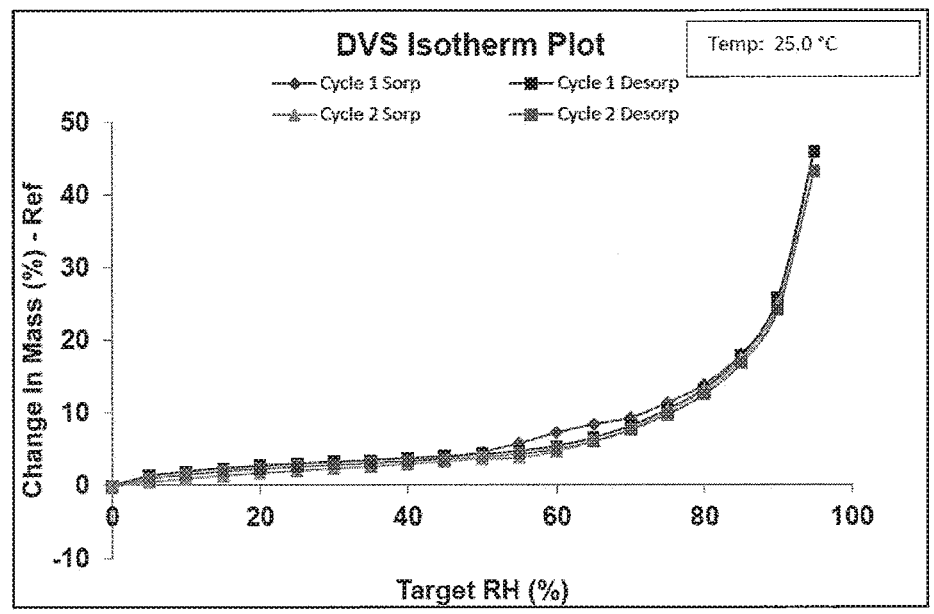
FIG. 3 is a characteristic Dynamic Vapor Sorption (DVS) curve for pyrroloquinoline quinine lithium salt crystal.
Figure 4:
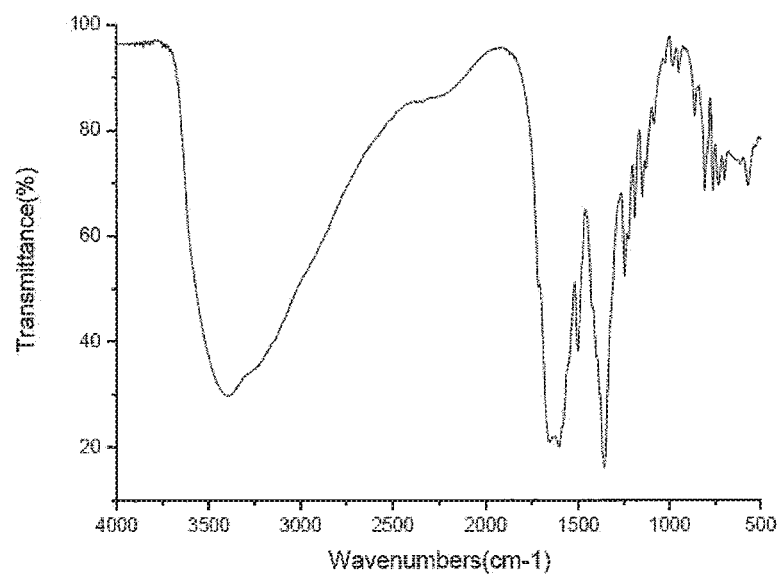
FIG. 4 is a characteristic infrared spectroscopy (IR) pattern for pyrroloquinoline quinine lithium salt crystal.

The obtained sample is measured by differential scanning calorimetry (DSC), dynamic vapor sorption (DVS) and infrared spectroscopy (IR), respectively, as shown in FIG. 2, 3, 4. The compound shows an endothermic peak of 93.33° C. in the differential scanning calorimetry (DSC) thermogram. It shows peaks around 3396.03 cm$^{-1}$, 1652.70 cm$^{-1}$, 1604.48 cm$^{-1}$, 1500.35 cm$^{-1}$, 1355.71 cm$^{-1}$, 1243.86 cm$^1$, 1147.44 cm$^{-1}$, 808.03 cm$^{-1}$, 761.74 cm$^{-1}$, 570.83 cm$^{-1}$ on infrared spectroscopy (IR) pattern. The compound stably exists as a nonahydrate by dynamic vapor sorption analysis. It forms monohydrate under the scope of relative humidity (RH) from 20% to 50%. It forms dihydrate under the scope of relative humidity (RH) from 70% to 100%. It could forms polyhydrate with further increased relative humidity (RH).

Example 2: Preparation of Crystalline Form B of Pyrroloquinoline Quinine Lithium Salt The obtained 10 mg of intermediate A of pyrroloquinoline quinine lithium salt from example 1 is dissolved in 0.5 mL of water, followed by adding 4 mL of isopropanol. The 0.5 mg of pyrroloquinoline quinine lithium salt crystal is obtained by standing overnight at room temperature. The obtained sample is measured by X-ray power diffraction, which shows the same peak pattern as example 1.

Example 3

Preparation of crystalline form B of pyrroloquinoline quinine lithium salt 10 mg of the crystalline form A of pyrroloquinoline quinine lithium salt (bought from Shanghai Rixin Biological Co., Ltd) is dissolved in 1 mL of organic solvent (the mixture of methanol and methyl tert-butyl ether with the ratio of 1:1). The 0.7 mg of crystalline form B of pyrroloquinoline quinine lithium salt is obtained by standing overnight at room temperature. The obtained sample is measured by X-ray power diffraction, which shows the same peak pattern as example 1.

Example 4: Hygroscopicity Comparisons of Crystalline Form a and Form B of Pyrroloquinoline Quinine Lithium Salt Under the scope of relative humidity (RH) from 5% to 95%, the hygroscopicity of the intermediate A of pyrroloquinoline quinine lithium salt and the crystalline form B of pyrroloquinoline quinine lithium salt from example 1 is measured by dynamic vapor sorption analysis. DVS curve indicates that the hygroscopicity of the intermediate A of pyrroloquinoline quinine lithium salt from example 1 is 25.3% and 32.6% under the relative humidity (RH) of 65% and 80%, respectively. Under the normal moist environment for storage, it shows highly hygroscopicity with a variety of 5-25%. The crystalline solid is not good. The hygroscopicity of the crystalline form B of pyrroloquinoline quinine lithium salt is 8.4% and 13.9% under the relative humidity (RH) of 65% and 80%, respectively. Under the normal moist environment for storage, it shows hygroscopicity with a variety of 5-10%. The crystalline solid is not good.

As used herein "basically pure" is that the crystal of the present invention preferably contains 90% or more of a crystalline substance, more preferably 95% or more, further preferably 96% or more, more further preferably 97% or more, especially preferably 98% or more, most preferably 99% or more of a crystalline substance, which used in X-ray powder diffraction (XRPD), raman spectroscopy, infrared spectroscopy (IR).

Example 5: A Pharmaceutical Composition Comprising the Pyrroloquinoline Quinine Lithium Salt Crystal Crystalline form B of pyrroloquinoline quinine lithium salt is mixed with magnesium stearate and crystalline cellulose according to the following description:

| | |
|---|---|
| Crystalline form B of pyrroloquinoline quinine lithium salt | 1.4 mg |
| Crystalline cellulose (Avicel PH102) | 116.2 mg |
| Magnesium stearate | 2.4 mg |
| Total | 120 mg |

120 mg of tablets of pyrroloquinoline quinine lithium salt is obtained by using tablet press machine with 7 mm of model.

Example 6: Animal Model for Biological Function of Pyrroloquinoline Quinine Lithium Salt Crystal Experimental Materials:

1. Wild-type mice (Shanghai Slac Laboratory Animal Co., Ltd, weights of mice are From 16 g to 18 g, male, totally 10 mice) for group 1.

2. APP/PS1 transgenic mice (Model Animal Research Center of Nanjing University, weights of mice are from 30 g to 40 g, male, totally 60 mice). Sixty mice are randomized to six groups (group 2 to group 7) with ten mice for each group.

Group 1: wild-type mice
Group 2: Model mice
Group 3: positive control of Aricept
Group 4: high dosage of pyrroloquinoline quinine lithium salt
Group 5: medium high dosage of pyrroloquinoline quinine lithium salt
Group 6: medium low dosage of pyrroloquinoline quinine lithium salt
Group 7: low dosage of pyrroloquinoline quinine lithium salt Solution Preparation:

High dosage group of pyrroloquinoline quinine lithium salt: 12 mL of solution A is obtained by dissolving 3.6 mg of crystalline form B of pyrroloquinoline quinine lithium salt in $ddH_2O$.

Medium high dosage group of pyrroloquinoline quinine lithium salt: 12 mL of solution B is obtained by diluting 6 mL of solution A with $ddH_2O$.

Medium low dosage group of pyrroloquinoline quinine lithium salt: 12 mL of solution C is obtained by diluting 6 mL of solution B with $ddH_2O$.

Low dosage group of pyrroloquinoline quinine lithium salt: 12 mL of solution D is obtained by diluting 6 mL of solution C with $ddH_2O$.

Aricept group: 0.15 mg/mL Aricept solution is obtained by grinding one tablet (5 mg) of Aricept into powder, followed by dissolved in 0.5% CMC (carboxymethylcellulose).

Experimental Instruments:

Morris water maze (Experimental video analysis system of Morris water maze, JLBehv-MWMG, Shanghai Jiliang Technology Co., Ltd)

Experimental Procedure:

Group 1 and group 2 are daily administrated by normal saline and group 3 to group 7 are daily administrated by drug solutions prepared above, with the dosage of 1 mL/100 g/day for continuous one month. From the fifth week, mice are training in Morris water maze, 30 minutes after drug administration. The training session lasts for 4 days. The probe test performed on the $5^{th}$ day. The Morris water maze statistics software is used to automatically record and analyze the swimming trace in the quadrant, time spent and path in target or opposite quadrant occupancy and times of crossing platform.

The data is indicated as average±standard deviation ($\bar{x}\pm SD$). The analysis of variance for a single factor is used for data difference statistics. Difference between groups is determined by P<0.05. Detailed results are demonstrated in table 1, 2, 3.

TABLE 1

Probe test on $5^{th}$ day: swimming path and time spent in target quadrant occupancy (n = 10, $\bar{x} \pm SD$)

| Group | Drug | Adjusted average distance of approaching to platform (mm) | time spent of IV quadrant (sec) |
|---|---|---|---|
| Vehicle | N.S | 579.7 ± 89.6 | 21.1 ± 4.8 |
| Model mice | N.S | 723.9 ± 85.1## | 12.6 ± 4.4## |
| Aricept | 1.5 mg/kg | 582.7 ± 104.4** | 21.7 ± 6.9** |
| High dose of PQQ-Li | 3 mg/kg | 572.5 ± 93.6** | 19.5 ± 8.5* |
| Medium high dose of PQQ-Li | 1.5 mg/kg | 605.6 ± 104.1* | 17.7 ± 5.9* |
| Medium low dose of PQQ-Li | 0.75 mg/kg | 674.9 ± 104.6 | 15.8 ± 7.6 |
| Low dose of PQQ-Li | 0.375 mg/kg | 762.6 ± 73.2 | 12.4 ± 4.2 |

P < 0.01 comparing with vehicle
*P < 0.05, **P < 0.01 comparing with model mice

TABLE 2

Probe test on $5^{th}$ day: swimming path and time spent in I quadrant occupancy of platform (n = 10, $\bar{x} \pm SD$)

| | | I quadrant occupancy of platform | |
|---|---|---|---|
| Group | Drug | Swimming path (mm) | time (sec) |
| Vehicle | N.S | 2829.7 ±983.3 | 11.2 ± 4.0 |
| Model mice | N.S | 1310.4 ±731.7## | 3.9 ± 2.6## |
| Aricept | 1.5 mg/kg | 2730.8 ±1485.3* | 9.3 ± 5.4* |
| High dose of PQQ-Li | 3 mg/kg | 2636.1 ±1091.5** | 9.2 ± 4.4** |
| Medium high dose of PQQ-Li | 1.5 mg/kg | 2653.3 ±1012.3** | 8.9 ± 4.0** |
| Medium low dose of PQQ-Li | 0.75 mg/kg | 2029.9 ±1133.1 | 6.4 ± 5.0 |
| Low dose of PQQ-Li | 0.375 mg/kg | 961.6 ± 560.7 | 2.8 ± 1.9 |

P < 0.01 comparing with vehicle
*P < 0.05, **P < 0.01 comparing with model mice

TABLE 3

Probe test on $5^{th}$ day: swimming path, time spent and times of crossing platform in I quadrant occupancy of platform (n = 10, $\bar{x} \pm SD$)

| Group | Drug | first time of crossing platform (sec) | times of crossing platform (sec) |
|---|---|---|---|
| Vehicle | N.S | 17.5 ± 19.2 | 2.2 ± 1.6 |
| Model mice | N.S | 49.1 ± 15.2## | 0.4 ± 0.5## |
| Aricept | 1.5 mg/kg | 30.7 ± 20.1* | 1.6 ± 1.3* |
| High dose of PQQ-Li | 3 mg/kg | 21.8 ± 17.8** | 2.3 ± 1.6** |
| Medium high dose of PQQ-Li | 1.5 mg/kg | 22.7 ± 19.6** | 2.2 ± 1.6** |
| Medium low dose of PQQ-Li | 0.75 mg/kg | 31.3 ± 22.6 | 1.6 ± 1.3* |
| Low dose of PQQ-Li | 0.375 mg/kg | 44.9 ± 17.1 | 0.8 ± 0.8 |

P < 0.01 comparing with vehicle
*P < 0.05, **P < 0.01 comparing with model mice

CONCLUSION

The crystalline form B of pyrroloquinoline quinine lithium salt has good dose-dependent effects on APP/PS1 transgenic mice shown in Morris water maze test. It could significantly improved spatial memory and cognitive impairment of APP/PS1 transgenic mice.

What is claimed is:

1. A pyrroloquinoline quinine lithium salt crystalline form B, characterized by an X-ray powder diffraction pattern with significant peaks at diffraction angles (2θ values) of about 6.222±0.2°, 7.379±0.2°, 7.941±0.2°, 23.631±0.2°; endothermic peak of the pyrroloquinoline quinine lithium salt crystal is around 90-96° C. in the differential scanning calorimetry thermogram; and the pyrroloquinoline quinine lithium salt crystal shows peaks around 3396.03 cm−1, 1652.70 cm−1, 1604.48 cm−1, 1355.71 cm−1 on infrared spectroscopy (IR) pattern.

2. The pyrroloquinoline quinine lithium salt crystalline form B according to claim 1, characterized by an X-ray powder diffraction pattern with more significant peaks at diffraction angles (2θ values) of about 24.044±0.2°, 25.497±0.2°, 27.541±0.2°, 30.736±0.2°, 32.306±0.2°; the pyrroloquinoline quinine lithium salt crystal also shows more peaks around 1500.35 cm−1, 1243.86 cm−1, 1147.44 cm−1, 808.03 cm−1, 761.74 cm−1, 570.83 cm−1 on infrared spectroscopy (IR) pattern.

3. The pyrroloquinoline quinine lithium salt crystalline form B according to claim 1, characterized by stably existing as a nonahydrate by dynamic vapor sorption analysis; the pyrroloquinoline quinine lithium salt crystal forms monohydrate under the scope of relative humidity (RH) from 20% to 50%, and forms dihydrate under the scope of relative humidity (RH) from 70% to 100%.

4. The pyrroloquinoline quinine lithium salt crystalline form B according to claim 1, characterized by endothermic peak of 93° C. in the differential scanning calorimetry (DSC) thermogram.

5. A method for preparing pyrroloquinoline quinine (PQQ) lithium salt crystalline form B according to claim 1 comprising step A and step B, wherein, Step A comprises:
mixing PQQ with lithium hydroxide (LiOH), wherein, the weight ratio of PPQ to LiOH is 4:1;
adding 16 mL ddH$_2$O;
stirring at 0-5° C. for 2 hours;
adding 8 mL acetonitrile;
continuing stirring for 1 hour to precipitate PQQ lithium salt form A;
filtering the PQQ lithium salt form A precipitates to obtain PQQ lithium salt form A; and Step B comprises:
(i) dissolving the PQQ lithium salt form A precipitate in water, wherein, the ratio of PQQ lithium salt form A to water is 20 mg:1 mL;
adding a solvent to form a complete mixture, wherein, the solvent is selected from the group consisting of tetrahydrofuran and isopropanol, and, wherein, the ratio of PQQ lithium salt form A precipitate to the solvent is 10 mg:4 mL; and
standing overnight at room temperature to obtain PQQ lithium salt crystalline form B;
or
(ii) dissolving the PQQ lithium salt form A precipitate in a 1:1 mixture of methanol and methyl tert-butyl ether, wherein, the ratio of PQQ lithium salt form A to the solvent mixture is 10 mg:1 mL; and
standing overnight at room temperature to obtain PQQ lithium salt crystalline form B.

6. A pharmaceutical composition comprising the pyrroloquinoline quinine lithium salt crystalline form B according to claim 1 and at least one pharmaceutically acceptable excipients.

7. The pharmaceutical composition of claim 6, wherein the excipients are selected from fillers, disintegrants, binders, lubricants and a combination of two or more thereof.

8. The pharmaceutical composition of claim 7, wherein the fillers are selected from starch, lactose, crystalline cellulose, dextrin, mannitol, oxidase, calcium sulfate and a combination of two or more thereof.

9. The pharmaceutical composition of claim 7, wherein the disintegrants are selected from carboxymethylcellulose and salt thereof, crosslinked carboxymethylcellulose and salt thereof, crosslinked polyvinylpyrrolidone, sodium carboxymethyl starch, low-substituted hydroxypropylcellulose and a combination of two or more thereof.

10. The pharmaceutical composition of claim 7, wherein the binders are selected from polyvinylpyrrolidone, hydroxypropyl methyl cellulose, starch slurry and a combination of two or more thereof.

11. The pharmaceutical composition of claim 7, wherein the lubricants are selected from magnesium stearate, calcium stearate and a combination of two thereof.

* * * * *